US008751031B2

(12) United States Patent
Sager

(10) Patent No.: US 8,751,031 B2
(45) Date of Patent: Jun. 10, 2014

(54) SYSTEM AND METHOD FOR MASS CUSTOM MANUFACTURING OF DENTAL CROWNS AND CROWN COMPONENTS

(75) Inventor: Robert D. Sager, Manhattan, KS (US)

(73) Assignee: Zircore, LLC, Manhattan, KS (US)

( * ) Notice: Subject to any disclaimer, the term of this patent is extended or adjusted under 35 U.S.C. 154(b) by 553 days.

(21) Appl. No.: 12/346,341

(22) Filed: Dec. 30, 2008

(65) Prior Publication Data

US 2009/0319068 A1 Dec. 24, 2009

Related U.S. Application Data

(63) Continuation-in-part of application No. 11/107,519, filed on Apr. 15, 2005, now Pat. No. 7,690,920, and a continuation-in-part of application No. 12/212,256, filed on Sep. 17, 2008, now Pat. No. 7,967,606, which is a continuation of application No. 11/023,950, filed on Dec. 28, 2004, now Pat. No. 7,445,449.

(60) Provisional application No. 61/099,566, filed on Sep. 24, 2008, provisional application No. 60/631,102, filed on Nov. 26, 2004, provisional application No. 60/566,855, filed on Apr. 30, 2004, provisional application No. 60/543,038, filed on Feb. 6, 2004.

(51) Int. Cl.
G06F 19/00 (2011.01)

(52) U.S. Cl.
USPC .......................................................... 700/96

(58) Field of Classification Search
USPC .............................................. 700/96; 433/24
See application file for complete search history.

(56) References Cited

U.S. PATENT DOCUMENTS

| 5,549,476 | A | * | 8/1996 | Stern | 433/223 |
|---|---|---|---|---|---|
| 6,049,743 | A | * | 4/2000 | Baba | 700/163 |
| 6,227,850 | B1 | * | 5/2001 | Chishti et al. | 433/24 |
| 6,463,344 | B1 | * | 10/2002 | Pavloskaia et al. | 700/98 |
| 6,558,162 | B1 | * | 5/2003 | Porter et al. | 433/173 |
| 6,886,462 | B2 | * | 5/2005 | Dick et al. | 101/483 |
| 6,901,356 | B1 | * | 5/2005 | Arita | 703/7 |
| 7,080,979 | B2 | * | 7/2006 | Rubbert et al. | 433/24 |
| 7,228,191 | B2 | * | 6/2007 | Hofmeister et al. | 700/98 |
| 7,408,336 | B2 | * | 8/2008 | Birmiwal et al. | 324/76.22 |
| 7,476,100 | B2 | * | 1/2009 | Kuo | 433/6 |
| 2002/0062461 | A1 | * | 5/2002 | Nee et al. | 714/28 |
| 2004/0204787 | A1 | * | 10/2004 | Kopelman et al. | 700/182 |
| 2006/0040236 | A1 | * | 2/2006 | Schmitt | 433/213 |
| 2006/0106484 | A1 | * | 5/2006 | Saliger et al. | 700/182 |
| 2006/0115794 | A1 | * | 6/2006 | Sager | 433/218 |
| 2008/0133031 | A1 | * | 6/2008 | Newman et al. | 700/73 |
| 2008/0222453 | A1 | * | 9/2008 | Bartz et al. | 714/28 |
| 2009/0088884 | A1 | * | 4/2009 | Yuan et al. | 700/110 |
| 2009/0088885 | A1 | * | 4/2009 | Yuan et al. | 700/110 |
| 2009/0089700 | A1 | * | 4/2009 | Gu et al. | 715/771 |
| 2009/0106604 | A1 | * | 4/2009 | Lange et al. | 714/45 |

* cited by examiner

Primary Examiner — Mohammad Ali
Assistant Examiner — Sivalingam Sivanesan
(74) Attorney, Agent, or Firm — Kutak Rock LLP; Bryan P. Stanley

(57) ABSTRACT

A Mass Custom Manufacturing System and methods are provided. A single master file is created for a restoration (or multiple restorations for a single patient) from a scan. Copings/cores, abutments and other companion pieces are designed using the master file through a deconstruction method allowing for simultaneous CAM of those pieces. A centralized system controls design and manufacturing, allowing the system to "learn" from feedback from the CAM operations of prior pieces and incorporate such feedback into the design phase.

5 Claims, 9 Drawing Sheets

SYSTEM AND METHOD FOR MASS CUSTOM MANUFACTURING OF DENTAL CROWNS AND CROWN COMPONENTS

CROSS-REFERENCE TO RELATED APPLICATIONS

This application claims priority pursuant to 35 U.S.C. 119(e) to U.S. Provisional Patent Application Ser. No. 61/099,566, filed Sep. 24, 2008, and is a continuation-in-part application of U.S. application Ser. No. 11/107,519 filed Apr. 15, 2005 and of U.S. application Ser. No. 12/212,256, filed Sep. 17, 2008, which is a continuation of U.S. application Ser. No. 11/023,950 filed Dec. 28, 2004 (now U.S. Pat. No. 7,445,449), which claims priority pursuant to 35 U.S.C. 119(e) to U.S. Provisional Patent Application Ser. No. 60/631,102, filed Nov. 26, 2004, U.S. Provisional Patent Application Ser. No. 60/566,855, filed Apr. 30, 2004 and U.S. Provisional Patent Application Ser. No. 60/543,038, filed Feb. 6, 2004, the entire disclosures of which are incorporated herein by reference.

FIELD OF THE INVENTION

The present invention relates generally to prosthodontic systems, methods and apparatuses. More particularly, the present invention is concerned with a process and system for mass custom manufacturing (MCM™) of dental crowns and crown components.

BACKGROUND OF THE INVENTION

Prior to the advent of the instant invention, prosthodontic manufacturing systems have been extremely labor intensive and time consuming, requiring a considerable amount of skilled (artisan) labor to custom fit prosthodontics for each case. Examples of prior art prosthodontic systems include the 3M/ESPE Lava™ System zirconium CAD/CAM-CNC Crown and Bridge Coping/Infrastructure(Core), the Camlog Implant System 2-part titanium-zirconium Ti-Ceramic Implant Abutment, and the Atlantis (owned by Astra Tech, a U.S. subsidiary of Astra Zenecca) custom CAC/CAM titanium or zirconium abutments. The Lava™ System creates its crown or bridge Cores from green-stage zirconium via a CAD/CAM CNC milling process followed by an over-night chemical infiltration and heat shrink transformation (sintering) process. The Camlog Implant System, as well as some other implant systems, utilize a two-piece standard product line implant abutment comprised of an upper manufactured sintered ceramic (zirconium) portion that requires subsequent custom modification by dental lab technicians in the field and a lower metal portion that affixes to the implant in the location in which a tooth replacement is necessary in the patient's mouth. The ceramic portion of the abutment, which is cement-bonded to the metal portion after the ceramic portion requires modification in the dental lab prior to beginning the construction of the crown coping (Core). The modified implant abutment affixed to a laboratory analog (implant duplicate) in the master stone laboratory model serve as the prepared tooth stump base for fabrication of a custom crown and bridge Core, such as a Lava™ crown and bridge coping/infrastructure (Core). The Atlantis system utilizes optically/laser scanned implant orientation information from a laboratory master stone model or patient to create a custom abutment from CAD/CAM instructions. A crown and bridge coping (Core) can then be made for the Atlantis or Camlog abutments conventionally by a lost wax artisan method (results in a metal crown and bridge Core) or from a separately scanned and CAD file generated CAM milling (results in a ceramic crown and bridge Core). It is noted that ceramic crown copings (Cores) can also be fabricated in an artisan method from built-up powder as in the Vita/Vident Inceram® zirconium System. It is noted also, all all-ceramic crown systems at present require some type of ceramic base coping/infrastructure (Core) and subsequent porcelain overlay to achieve the desired contours of the tooth that is being replaced. But in all cases, by prior art, Implant abutments must be fabricated before Crown and Bridge Cores can be designed and fabricated, and finished Crowns can only be fabricated after the completion of the Core and its geometry is known by post fabrication inspection.

In the conventional system, when a patient requires a tooth replacement, a three-dimensional stone model of the patient's mouth is prepared from a master impression. If a two-piece abutment such as the Camlog Implant System's Ti-Ceramic Abutment described above is to be utilized, a lab technician will use the stone lab model of the patient's mouth to fit and manually modify the sintered zirconium portion of the two-part abutment (or coronal portion of any all metal abutment) and then affix it to the metal portion of the abutment into the appropriate implant analog location in the model. The ceramic portion of the abutment is shaped so it is appropriate for the location and orientation in which it will best support the final crown positioned within the patient's mouth. Once the ceramic portion of the abutment is modified to its final shape, the abutment, which is located in the model, is scanned. Using data from the scan about the shape and orientation of the abutment, as well as the existing teeth surrounding the position of the abutment, the necessary shape of a crown coping (Core) is determined and the crown coping (Core) is manufactured. In the context of the Lava™ System, a Computer Numeric Control (CNC) milling machine is utilized to manufacture the coping/infrastructure (Core) by milling a green-stage zirconium Lava™ block into a coping/infrastructure (Core) that is then heat treated. Once the coping is completed, and built-up with porcelain to resemble a natural tooth, the entire piece (coping and abutment) is ready for placement in the patient's mouth. The crown coping/crown may be cemented conventionally (like any crown to a tooth) to the installed abutment.

The prior art system described above is very time consuming, as it requires a considerable amount of labor and time to modify the abutment and then separately manufacture the coping (Core) based upon the shape of the modified abutment, and then start on another unrelated process to build the Core to its final geometry with porcelain. In some cases, the ceramic portion of the abutment requires considerable modification due to its orientation within the patient's mouth such that a relatively small surface of the abutment remains for mounting of the coping (Core). It is noted that a ceramic infiltrated sintered abutment is extremely hard to cut compared to green stage zirconium material. In addition, the prior art system results in substantial waste of materials as the ceramic abutment and the coping (Core) are manufactured independently and/or by different processes and/or materials. Certainty of final geometry, size and precision is lost if shaping is accomplished in the green stage zirconium, because unpredictable shrinkage often exceeding 20% will result in subsequent required heat shrink transformation treatments. Therefore, it would be beneficial to provide a system for simultaneously manufacturing a custom dental crown coping/infrastructure (Core) and implant abutment (or ceramic portion of the abutment if two piece) to reduce the amount of labor, time and materials.

As the conventional system for designing dental restorations described above requires that a dental restoration be designed (and built) in a derivative, linear manner from the ground up, i.e. first design the abutment, then design the coping (Core) to fit the abutment, manufacturing processes and systems have been extremely limited. Improvements in technology have been interspersed throughout the process at various levels to replace certain functions, but the system as a whole remains relatively unchanged and inefficient. In many cases, the technology has increased the overall production time for a dental restoration, because it is being added to a manufacturing process rather than designed as part of a manufacturing process and/or supporting the manufacturing process. Mass production has generally occurred at the pre-made prosthetic component level rather at the end product production level. As such manufacturers will mass-produce abutments of several shapes and/or sizes so that a suitable piece may be selected for the particular situation and require minimal modification. As each patient's mouth is different, every dental restoration is unique. Thus, having a finite number of options of shapes and sizes of mass-produced abutments requires that the abutment be modified for the particular application (as is described above). Even the Atlantis custom implant abutment starts the process with an inventory of individual partially-machined implant brand-specific blanks, to produce final custom abutments. Even though the Atlantis custom implant abutment is the product of a modern CAD/CAM design and milling process, it still has no coordinated follow-on Core process. Once modified, the abutment must be scanned and a custom coping (Core) may be machined by another system. This conventional system is best described as a custom mass-production system, as certain parts may be mass produced to make customization easier, but those parts must still be modified or customized before they can be utilized. Therefore, it would be beneficial to provide a system and method for Mass Custom Manufacturing of dental restorations and/or components thereof.

Furthermore, each component of a restoration in the custom mass-production system of the prior art discussed above is still designed and made individually. The prior art custom mass-production system is really a combination of multiple systems, as opposed to a single system of production. For example, once an abutment is modified by a dental technician and scanned, the data from the scan of the abutment is used to manufacture a coping (Core) that fits the modified abutment. The data file used to machine the coping (Core) is no longer used. And it has not been archived in any manner to feed some follow-up production process. In the case of modern press ceramic application method, a wax-up of the final restoration is made on top of the coping (Core), and the entire unit is sprued and invested in a lost wax burnout method for later press packing and baking of ceramic material. The wax is melted out of the mold and the mold is used to press the porcelain veneer material to make the final shape of the restoration. It is noted porcelain may also be layered and baked in an artisan method also to achieve a final all-ceramic restoration, alternative to the press ceramic method. But the point to be made is in prior art, the coping (Core) itself is always designed and manufactured individually without any direct subsequent relation to follow along processes. The coping (Core) will be designed by a CAD user, and the CAD file will be sent to a CAM operator to manufacture the piece that has been designed, and all processes to follow are independent of the CAD/CAM process of making the coping (Core). In some instances, the CAD user will design a piece that is impossible for the CAM to mill, and all subsequent processes are thereby totally thwarted until the Core mill is resolved. In prior art it is entirely possible that all components all the way back to the implant abutment, may have to be remade, because of the failure of designing the first component to the dimensional requirements of the actual condition in the mouth and on the master model. It is noted that each process, although technologically embellished, in prior art is driven by individual and non-interrelated design, engineering and manufacturing processes. Therefore, it would be beneficial to provide a system and method for mass custom production (a Mass Custom Manufacturing System) that provides increased efficiencies over the custom mass-production system of the prior art.

SUMMARY OF THE INVENTION

A principal object of the instant invention is to provide a system for simultaneously or mechanico-sequentially, designing and/or fabricating custom dental crown and bridge coping/infrastructures (Cores) and one or more other companion/collateral pieces (such as an implant abutment or crown mold) to reduce the amount of labor, time and/or materials. The process is accomplished by integrating, sharing and interpreting stored CAD/CAM digital job information, dental design and algorithms, CNC and CAM programs and advanced data warehousing and adaptive learning to achieve optimized custom milling results. Another object of the invention is to provide a system and method for mass custom production (Mass Custom Manufacturing, in anagram, MCM) of dental restorations and/or components (Cores, temporary crowns, abutments, molds to make crowns, models, etc.) thereof. Still another object of the invention is to provide a system and method for Mass Custom Manufacturing that provides increased efficiencies over the custom mass-production system of the prior art.

Objects of the instant invention are accomplished through the use of a mass custom production (Mass Custom Manufacturing, MCM™) system that provides for reduced handling and the efficient use of labor, material and machinery in the manufacturing process to ensure optimized production output. The MCM™ (Mass Custom Manufacturing) System utilizes centralized, integrated and automated scan, design and manufacturing of all crown and bridge Cores, companion (i.e. components that mate together with each other) and collateral (i.e. peripheral pieces, such as molds, that are used to make a final piece that mates together with other components of a restoration) Core components (including, but not limited to, implant abutments, models, crown molds, composite resin temporaries) production. All crown and bridge Cores, companion and collateral components are made, in a preferred embodiment, only from "end-stage" materials that do not require material-altering post-production processes. In another preferred embodiment, a unique, specialized packaging/transfer system that includes a multiple-compartment box, labels, and a data-collection/transfer system, is used to regularize case management through the scan, design and manufacturing process of the instant invention.

The system and method for Mass Custom Manufacturing of dental restorations, crowns and/or components (Cores/copings, temporary crowns, abutments, molds to make crowns, models, etc.) of the instant invention utilizes a master data file that is created by a centralized computer control system, In a preferred embodiment, the master data file is created through a deconstruction design method. The master file is created for a restoration (or multiple restorations for a single patient) through a 3D scan, or other digital, electronic or virtual input of information relating to the real condition of the a patient's mouth (i.e. scanning a patient's mouth, impression taken from the mouth, or a model constructed from an impression taken from the mouth). Cores, abutments and other companion/collateral pieces are designed through a CAD (or other similar type design system) software application of the instant invention using the master file which allows for simultaneous CAM (computer automated manufacturing) of two or more pieces. The centralized system controls design and manufacturing, allowing the system to "learn" from feedback from the CAM operations of prior pieces and incorporate such feedback into the design phase.

One exemplary embodiment of the inventive system utilizes a two-piece abutment similar to that described above (until such time as the material and process allow one piece ceramic/zirconium, titanium or other abutments). The metal insert portion of the abutment is a standard piece. The ceramic portion of the abutment becomes a custom made piece, which is manufactured at the same time the coping (Core) is manufactured. When a patient requires a tooth replacement, an impression and/or master stone model of the patient's mouth is prepared. The model and/or impression would have an implant analog in place for missing teeth desired to receive implant supported restorations. The impression/model will then be boxed up by special protocol using the packaging/transfer system of the instant invention and shipped to a central Mass Custom Manufacturing location of the instant invention. Upon receipt at the Mass Custom Manufacturing location, the model is scanned and the scan data is used to create a master file for the particular restoration. The scan provides data about the orientation of the implant analog within the model of the mouth and also data about the existing teeth surrounding the position of the abutment. The data from the scan, along with stored data about the standard shape of the metal insert to which the ceramic portion is to be mounted, is used to determine and design the appropriate shape for the ceramic portion of the abutment. At the same time, the shape of the coping/Core (or other companion or collateral components) is internally designed, using the data so that the coping (Core) will fit over the designed ceramic portion of the abutment.

As discussed with respect to the prior art, cutting the ceramic pieces in the green stage is much easier to accomplish than cutting once the pieces have been sintered. Nevertheless, the sintering process itself is an additional time consuming step that is required when working with green stage pieces and the shrinkage of organic shapes such as dental restorations occurs in a nonlinear manner that is difficult, if not impossible, to quantify in any accurate and reliable equations. Therefore, in the instant invention the pieces are milled from "end stage" materials (requiring no post production material processing or transformation) such as factory sintered and HIP'd blocks or rods of zirconium or medical grade pure titanium or any other suitable end stage material now known or later discovered). Cutting of the factory sintered block is slower than cutting from a green stage blocks; however the additional sintering step is eliminated. The use of a factory sintered and HIP'd blocks provides additional advantages over the use of a greenware block, such as allowing larger pieces to be milled from a single block or rod (i.e. full arches versus single crowns or bridges). In one preferred embodiment, as is discussed above, any and all crown and bridge Cores, and/or companion and collateral components are made only from "end-stage" materials that do not require material-altering post-production processes, such as factory sintered HIP'd (Heat and Isostatic Pressure).

In one preferred embodiment of the instant invention, in which the ceramic portion of the abutment is milled from a factory sintered HIP'd block, a custom ceramic portion of the abutment and custom crown Core are made for use with an off-the-shelf lower abutment portion, such as the lower metal portion (Ti-base) of the Camlog Implant System discussed above. Information regarding the size and shape of the off-the-shelf pieces are stored in a data file or library accessed by a milling machine (such as a DCS milling machine) or otherwise accessed as part of the CAD process (i.e. by the central control system). The implant analog of the Ti-base is placed in a master model implant analog and the model is scanned to obtain data about the orientation of the base within the model and data about the existing teeth surrounding the position of the base within the model. The data from the scan is combined with the stored size and shape information regarding the Ti-base to design a custom ceramic abutment portion part to fit over the Ti-base and a custom crown Core to fit over the custom ceramic abutment portion. The custom ceramic abutment portion will be designed to have predetermined minimum dimensions based upon the size and shape of the Ti-base being used. In most instances however, the actual custom ceramic abutment portion will have dimensions greater than the library-stored "minimum", thus the dimensions of the custom ceramic abutment portion will include a virtual wax-up from the minimum dimensions. Once the final dimensions for the custom ceramic abutment and the custom crown Core are determined by wax-up software, the ceramic abutment and Core pieces are milled. In one preferred embodiment, both pieces are milled from a single block of material. In an alternative embodiment, both pieces are milled simultaneously from different blocks of material on different machines as part of the Mass Custom Manufacturing System of the instant invention.

In prior art systems, the custom dental crown Core and infrastructure (abutment) and other companion or collateral component pieces are manufactured from the ground up. The abutment is designed first and the Core is designed to fit the abutment. In the instant invention the custom dental crown Core and infrastructure can be manufactured from the ground up by first determining the shape and orientation of the abutment and then determining the shape and orientation of the Core (and/or other companion or collateral pieces). Alternatively, the custom dental crown coping and infrastructure of the instant invention can be designed and manufactured ("deconstructed") from the end product. In such a manner, the model is scanned and the shape and orientation of the final crown is determined, visualized or obtained by the software of the centralized control system of the instant invention, then the underlying structures are designed by the system by subtracting away or deconstructing from that shape to leave the substructure shape. In such an embodiment, the part of the final shape that is subtracted is determined to maximize the aesthetic appearance of the final restoration by concealing the substructure. The thickness for the crown is subtracted from the final shape of the crown to determine the shape and orientation of the Core. The thickness of the Core is then subtracted from the shape of the Core to form the shape and orientation of the abutment.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION OF A PREFERRED EMBODIMENT

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The inventive system and method of Mass Custom Manufacturing of dental crowns and crown components shall be described herein in connection with an embodiment that utilizes a deconstructive design and manufacturing method. Nevertheless it will be appreciated that alternative design and manufacturing methods may be utilized without departing from the spirit and scope of the instant invention.

Figure 9:
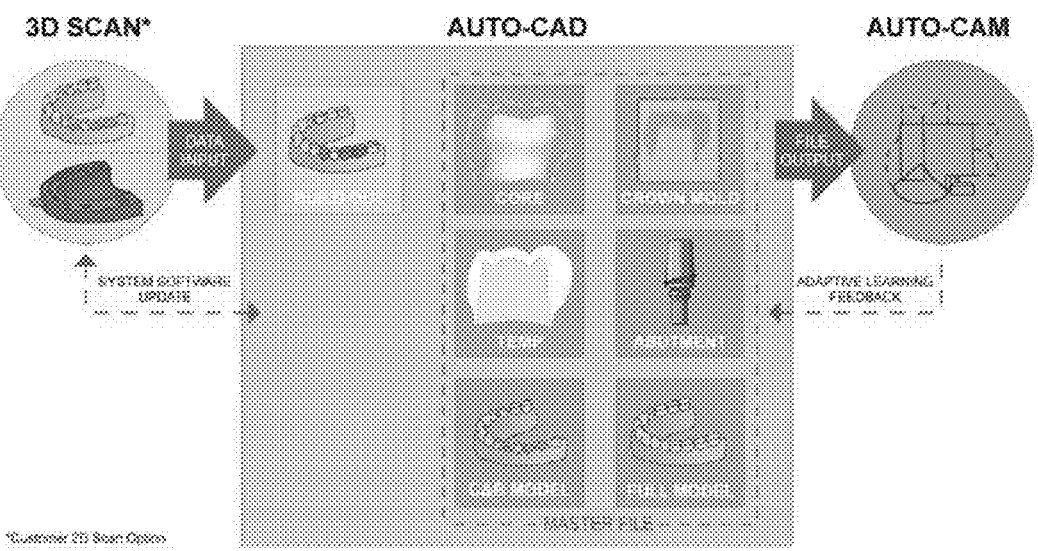
FIG. 9 shows a schematic of the Mass Custom Manufacturing System of an embodiment of the invention.
Figure 10:
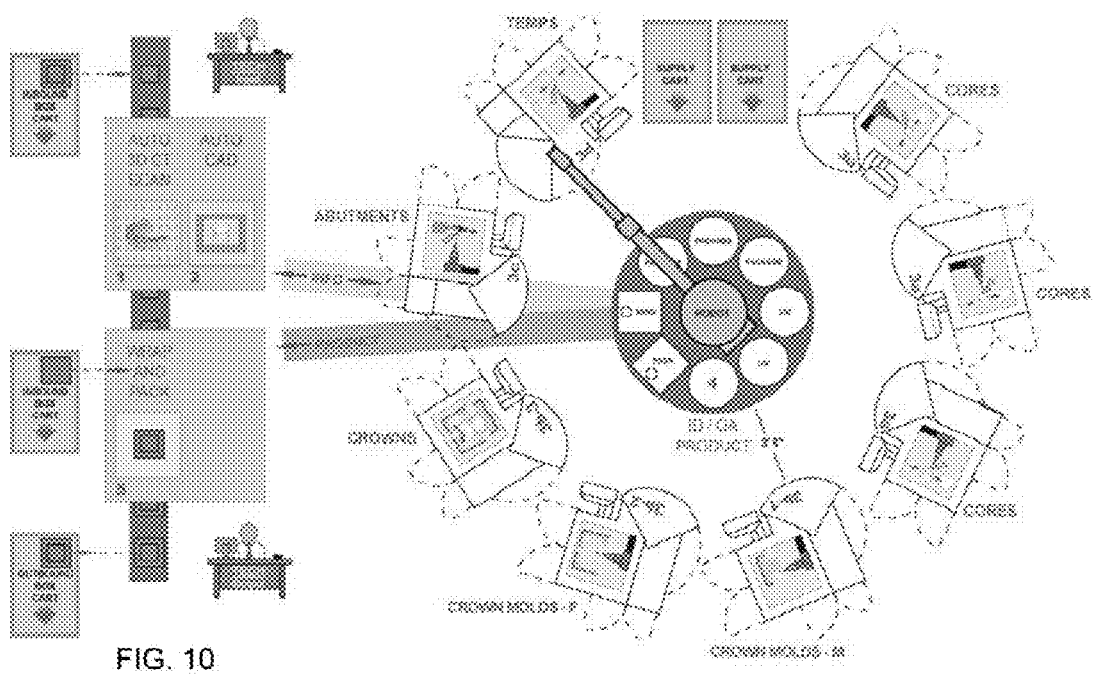
FIGS. 10 and 10a show schematics of preferred embodiments of several manufacturing facilities incorporating the Mass Custom Manufacturing System of FIG. 9.
Figure 10A:
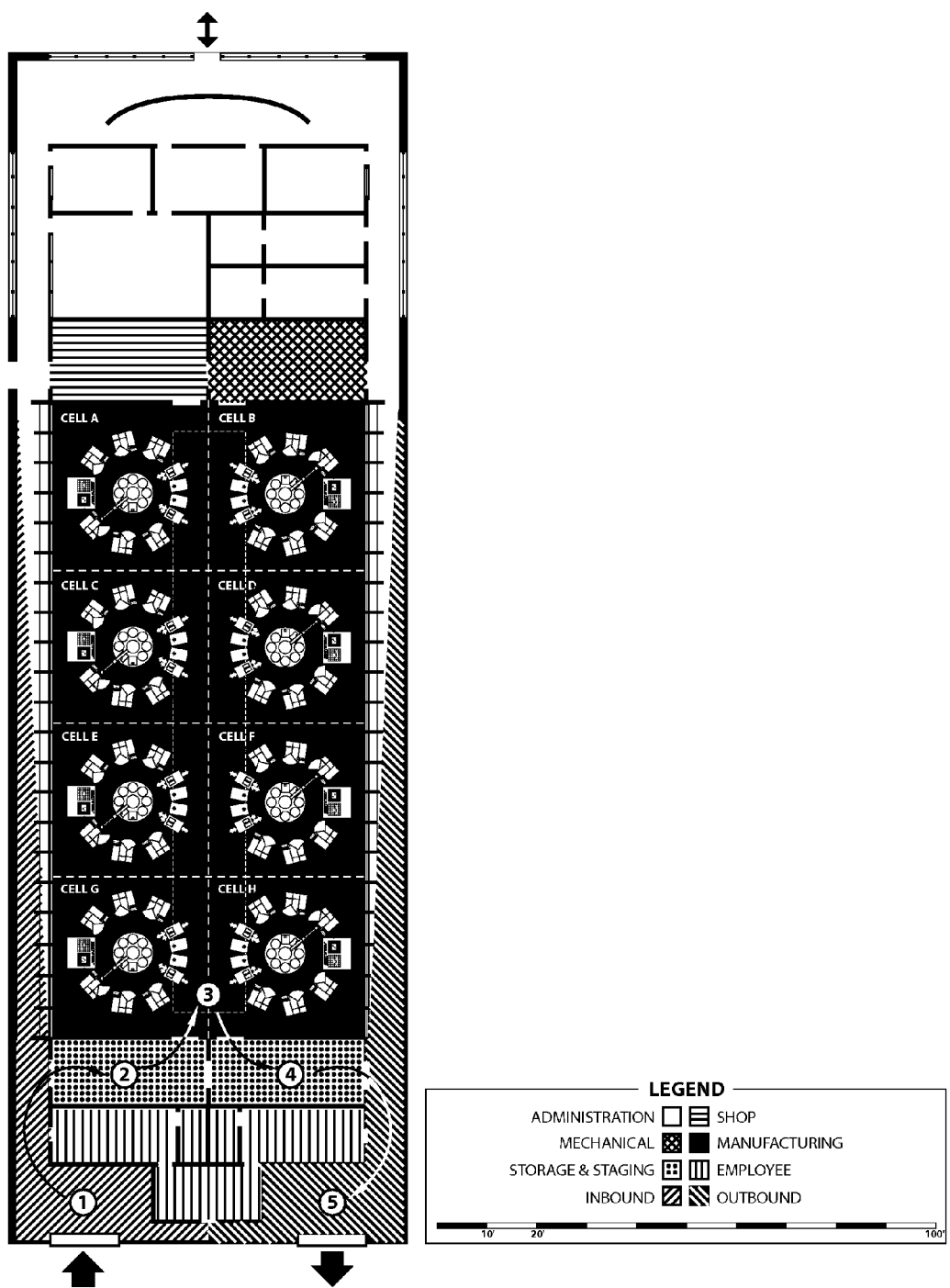

Referring to FIGS. 9, 10 and 10a a Mass Custom Manufacturing System of the instant invention is shown and described. The system re-orders and converges multiple dental manufacturing SCAN/CAD/CAM files of information to facilitate simultaneous and/or divergent mass, custom production of crowns and crown components. The inventive system provides an automated CAD/CAM dental manufacturing system that creates a virtual replacement tooth master file that directs subsequent deconstructive component design.

As is shown in FIGS. 9 and 10, a model (or other representation of the real condition) of a patients mouth is prepared. The model will include the missing tooth location, tooth stump, abutment base, preparation or condition at the location in which the restoration is to be located. In the preferred embodiment the model is shipped from the dentist that prepared the model to the dental lab manufacturing facility that incorporates the Mass Custom Manufacturing System of the instant invention. In one embodiment, the model is shipped through the use of the packaging/transfer system shown in FIG. 11 and described in further detail below. This allows the lab to control the inputs. Nevertheless, it will be appreciated that the model (or other representation of the real condition of the patient's mouth) may be scanned (or otherwise converted into digital/electronic file data) at any location, including the dentist's office. In the embodiment shown, the model is received in the lab and a label on the packaging/transfer system is scanned to provide data regarding the contents of the package. The model is then scanned (either 2D or preferably 3D scan) at the dental lab facility to initiate data for the creation of a master data file. In a preferred embodiment, the master data file is created using the automated CAD software described above. The software utilizes the scan data and adds to, modifies or updates the master data file to design the restoration components. First, the software will replace any missing teeth using the deconstructive design process discussed in greater detail below. As is discussed in further detail below, the software will determine a final external shape for the missing tooth. Then the software will replace any prepared teeth with a full build-out again by determining the final external shape for the prepared teeth. The deconstructive process is then utilized to make the substructure components of the restoration by subtracting away the thicknesses from concentric components. As is shown in FIGS. 9 and 10, the master file may contain designs for and/or may be utilized to design any component (companion or collateral) of the dental restoration, including but not limited to Cores, crown molds, temporary restorations, abutments, crown and bridge models, full models, etc. It will be appreciated, that the abutment utilized in connection with the system of the instant invention may be a single piece abutment or a two-piece abutment as is shown in the embodiment discussed herein. If a single piece abutment is utilized, the Core will fit directly onto the abutment. If a two-piece abutment is utilized the restoration Core (coping/infrastructure) will fit onto the ceramic portion of the abutment, which itself fits onto the metal insert portion of the abutment.

Because the master file includes scan data regarding the operative arch and preparation area, as well as the software generated (virtual) final external shape of the restoration(s) to fit over the preparation area(s), the master file may be utilized to make any of the components (or subcomponents) of the restoration described above. This is possible even at a time after the master file has been utilized to create only certain components. For example, a master file might initially be utilized to design and manufacture a Core (coping/infrastructure). If it is later desired to manufacture an abutment, the master file (which has been stored/archieved) may be accessed by the software and the data regarding the final restoration shape and/or the final Core shape may be utilized in a deconstructive manner to design the abutment to fit within the Core (i.e. by subtracting away a thickness for the Core, based upon user defined or predefined criteria for Core thickness, shape, etc.).

Once all component pieces that are desired to be manufactured have been designed, one or more output files are created by the software based upon the master file data for use by an (one or more) automated CAM machine(s). In one preferred embodiment, referring to FIG. 10, multiple automated CAM machines are located around a central robot. A central control system controls the robot and all the CAM machines. In a preferred embodiment, the automated CAD design software of the instant invention is separate from the automated CAM software of the central control system. Nevertheless, it will be appreciated that a single software application may control both the CAD and the CAM processes of the instant invention. In a preferred embodiment, in which a separate software application controls the central processor of the CAM, the CAD software output includes multiple output files, a single file for each component piece that is to be manufactured. In an alternative embodiment, the output file includes a single file from which individual component designs may be separated by the CAM control system. Although described herein as a deconstructive process, it will be appreciated that the master file data of the instant invention in an alternative embodiment is made through a ground up construction process, in which the shape for the center most component (i.e. the abutment or implant) is first designed, and then the core/coping is designed to fit the implant, and then the veneer is designed to fit over the Core, etc. In either embodiment, the master file includes data to allow two or more pieces to be simultaneously manufactured.

The control system sends control commands to the surrounding CAM machines to make the desired components. As is shown in FIG. 10, the control system may simultaneously (or in any order desired) control the manufacture of any number of restoration components. The manufacturing facility shown in FIG. 10 includes CAM machines capable of manufacturing abutments, temporary crowns, Cores (copings/infrastructures), crown molds (in the embodiment shown, male and female portions of a two-piece mold), and ultimately crowns. In the embodiment shown, the crowns must be pressed using the two-piece crown mold. Thus, it will be necessary to manufacture the crown molds prior to pressing the crown veneer. All other components may be manufactured in any order or simultaneously. In a preferred embodiment, the CAM machines of FIG. 10 utilize a continuous production system as is described in U.S. application Ser. No. 11/023,950. Nevertheless, it will be appreciated that any CAM machine or other manufacturing process now known or hereinafter developed may be utilized without departing from the spirit and scope of the instant invention. For example, pieces may be injection molded, milled, built-up, sintered, welded, etc.

Once components are manufactured, the articulated robot arm removes the pieces from the CAM machines, runs the pieces through an identification and/or quality insurance station (automated or manual), and packages the pieces for shipment. The completed pieces are then wrapped, packed (automated or manual) and shipped to the dentist that had sent the model to the manufacturing facility. In addition, the dentist can be provided the master file, or requested data from the master file for use in completing the restoration. For example, a dentist, or technician may wish to customize the veneer. The software of the instant invention can provide information regarding the amount of porcelain necessary for the customization, or how much is needed to make the piece look opaque.

Referring to FIG. 10a, a manufacturing facility of another preferred embodiment of the instant invention is shown. In the embodiment shown in FIG. 10a, the majority of labor is focused on customer relations and automated manufacturing management, rather than on artisan fabrication. This paradigm shift allows technology to drive the manufacturing process rather than be ancillary to it. The facility shown in FIG. 10a consists of a central transparent clean-room MANUFACTURING (3) area that is flanked on two sides by "action" ADMINISTRATION (2, 4) areas that interface manufacturing tech support and administrative customer support. The INBOUND/ADMINISTRATION (1) area mates customer job items with production and manages SCAN, CAD and input matters. OUTBOUND/ADMINISTRATION (5) focuses on all CAM, quality assessment and output matters.

MANUFACTURING is supported on one side by an INBOUND/RECEIVING area where job items received from customers are logged in, and STORAGE AND STAGING areas where raw materials and job items are organized coming and going, and an OUTBOUND/SHIPPING area for dispatch of newly manufactured items and job items being returned to customers. All INBOUND and OUTBOUND customer job items and raw materials are moved on carts in and about of the MANUFACTURING facility.

A SHOP area for equipment maintenance and a MECHANICAL area for equipment and control systems, supports the MANUFACTURING area from the fourth side. All manufacturing equipment are "plug and play" interchangeable and movable in and out of the MANUFACTURING area. In the embodiment shown in FIG. 10a, the MANUFACTURING area includes multiple robot stations similar or the same as are shown and described in FIG. 10.

In preferred embodiments of the instant invention, all materials for manufactured goods are continuously tracked from the mine to the mouth. All Customer job items are traced real-time from the mouth through manufacturing back to the mouth. All finished manufactured goods are Certified. Management's goal is to continually optimize automation of the manufacturing processes and consistency of manufactured goods.

In a preferred embodiment of the inventive manufacturing system, all components are manufactured from end state materials (i.e. materials of same consistency during manufacturing as when piece is completed) as opposed to green state materials, or are made from green state materials through the use of an exacting mold of the final piece such that the material assumes end state properties in through the precision mold. This ensures the dimensional integrity of the pieces, allows pieces to be made simultaneously and minimizes the calculations necessary to design a piece, in that it is not necessary to factor in shrinkage (or expansion) of materials.

The manufacturing system of the instant invention converges technologies such as scanning input, CAD design and CAM manufacturing together in an automated, centrally controlled system to allow for integrated, simultaneous manufacturing of two or more pieces of a dental restoration. The central control allows for adaptive learning by the system as information is exchanged between the CAD and CAM phases. For example, if a piece is designed in the CAD process that cannot physically be manufactured by the CAM equipment, the central control system will update (in addition to routine software updates coming from a program designer) the design file or database (or libraries) of the CAD system in real time to prevent the CAD system from making the same or similar design error in the future. As another example, the central processor can utilize prior design and manufacturing information to narrow predetermined design parameters. For example, after multiple design and manufacturing processes are completed, it may be learned that the diameter of stock material for a component such as a crown should be changed, or that one of multiple diameters of stock material is not necessary, due to the fact that all pieces end up being made of certain dimensions. Software control algorithms of the central control system continuously monitor the CAD and CAM phases, actions taken in those phases, evaluates design parameters and stores design parameters in a continuously updated database, to allow for the adaptive learning discussed above. For example, one control algorithm is programmed with or accesses data regarding the diameters of rod stock available for manufacturing certain pieces. The control algorithm continuously accesses and monitors data regarding actual components that are designed and manufactured by the central control system, and evaluates that data in real time to make a determination as to the proper diameter of material to be used to make the next piece that is being designed and/or manufactured. Other algorithms monitor and update libraries of data regarding preferred component designs for specific situations. For example, design libraries of specific sizes and shapes for replacement teeth are continuously updated with data regarding the specific components that are designed and manufactured. This allows the system of the instant invention to capture and utilize trends of tooth numbers of missing teeth and teeth that are heavily worked upon to update the library of shapes and sizes that will be utilized in designing components through the instant invention.

As opposed to the divergent, linear systems of the prior art, in which multiple individual manufacturing systems are utilized to make a single restoration, the instant invention provides a single system for Mass Custom Manufacturing. Unlike traditional mass production systems, in which all pieces are made the same, the instant invention allows for mass production of custom pieces.

Figure 11:
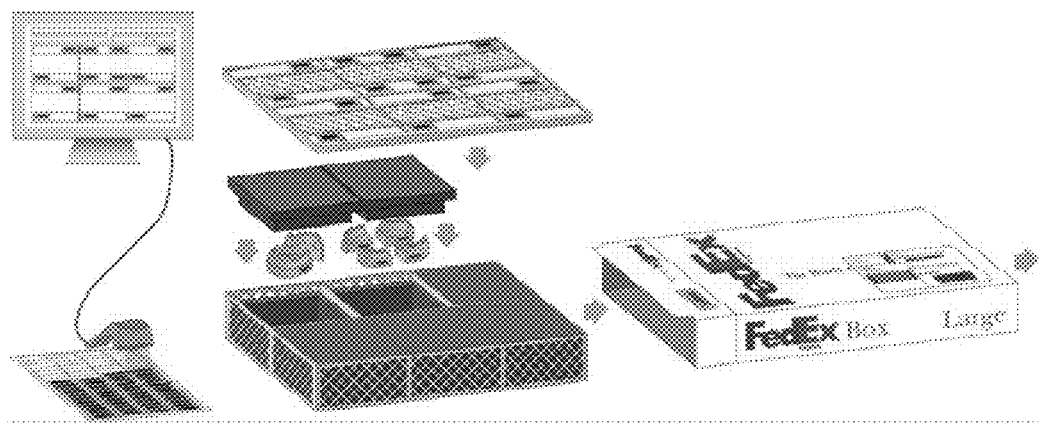
FIG. 11 shows a packaging/transfer system of the instant invention.
Figure 11:
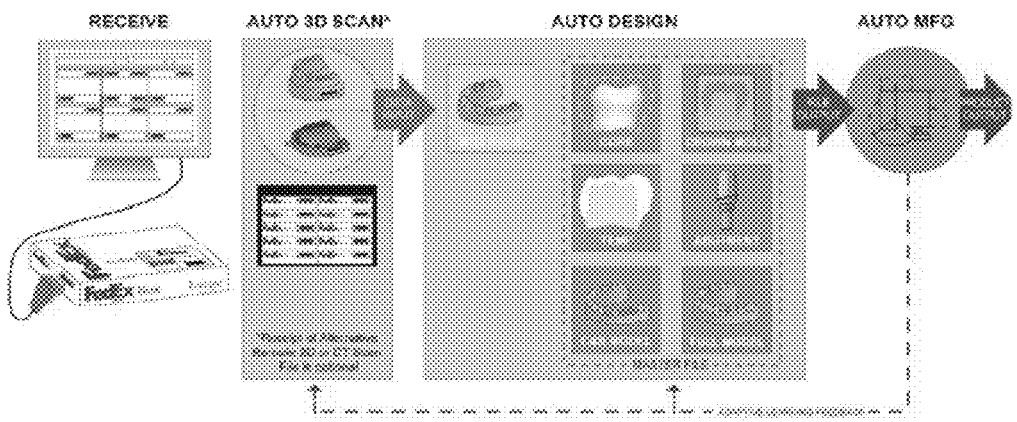

Referring to FIG. 11, a packaging/transfer system of a preferred embodiment of the instant invention is shown. The dentist lab person (or other person) that creates the model of the patient's mouth places a label sticker on the model from a sheet of labels of the instant invention. The lab person then accesses a computer program of the instant invention that includes a diagram of a compartmentalized shipping box of the instant invention. The shipping box of the instant invention includes multiple compartments that are each designed to accept and hold two full arch models or four quadrant models. The lab person scans the label using a scanner that operates with the computer program. The label includes a unique identification code, such as a bar code. The lab person associates that unique code with the proper location shown in the diagram of the shipping box in which the model has been placed. A separate unique identification label is placed on the cover of each compartment to collectively link all models within the shipping box to this "sub-totaling" label. Another unique, master label is placed on the outside of the shipping box which links all sub-totals and the individual model labels together. A master data file is transmitted from the computer program of the dentist lab person to the centralized lab of the Mass Custom Manufacturing System of the instant invention. The master data file includes information regarding all of the above labels that have been scanned in or otherwise input into the computer program during packing. Once the package is received at the centralized lab, the master label is scanned, which allows the control system of the instant invention to identify and access the appropriate master data file. The master data file will include information regarding the identification of each individual model or model portion included within the box, including location within the box, individual instruction regarding each model (i.e. shipping requirements, billing instructions, credit card information, additional services, specific pieces that must be manufactured—abutment, crown mold, models, temporaries, material to be used (i.e. zirconium or titanium), instructions of segmentations for bridges or between two teeth with an edentulous space, or if a double abutment termination and/or exactly from what tooth to what tooth the bridge goes to and from). All such data is input by the person packing the box and transmitted to the centralized lab. The master data file may be transmitted by electronic media such as email or over the internet, or alternatively may be included via portable media such as a disk or flash drive. In one embodiment, the master file data is encoded into the master label itself, such as through an encoded chip, or through a unique encoded printing system for the master label. After obtaining the master data file information, the model(s) within the box are scanned. The design of the box of the instant invention allows a 3D scan to be accomplished automatically by a robot that manipulates and opens the box, knowing the orientation of the box and location of the model within the box. The 3D scan may be accomplished without removing the model(s) from the box.

Figure 1:
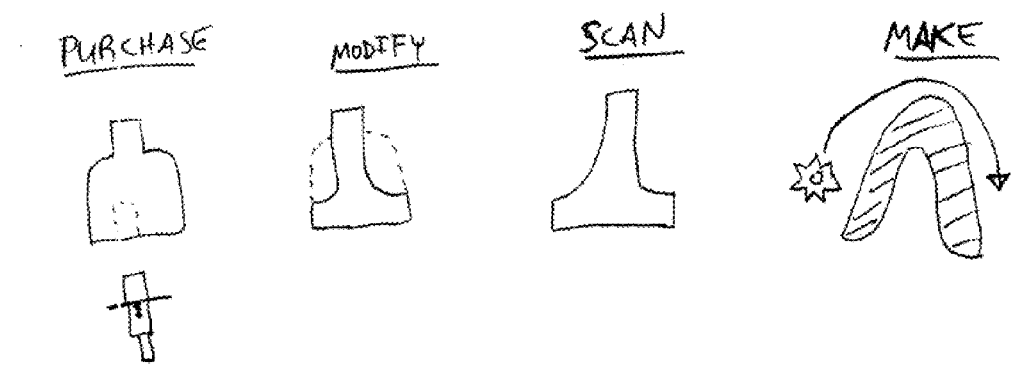
FIG. 1 is a schematic of a method of manufacturing custom crown copings and infrastructures of the prior art.

Referring to FIG. 1 a schematic of a method of manufacturing custom crown Cores and infrastructures of the prior art is shown in which dental crowns and crown components are manufactured from the ground up. As is shown in FIG. 1, the manufacturing method of the prior art begins with the purchase of a two-piece abutment from a manufacturer. The analog of the abutment is located in a model of the patient's mouth and the ceramic portion of the abutment is then modified by a technician to a shape that is appropriate for the location and orientation in the patient's mount. Once the ceramic portion of the abutment is modified to its final shape, the abutment analog, which is located in the model, is scanned. The data from the scan about the shape and orientation of the abutment, as well as the existing teeth surrounding the position of the abutment, is then used to manufacture a crown Core (coping/infrastructure).

Figure 2:
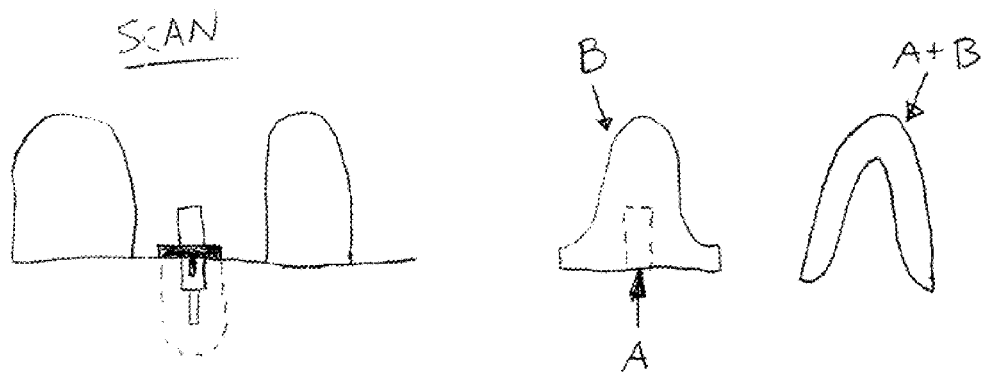
FIG. 2 is a schematic of the method of manufacturing custom crown Cores and infrastructures utilizing a deconstructive method.

Referring to FIG. 2 is a schematic of the method of manufacturing custom crown Cores (copings/infrastructures) and other components through a deconstructive method is shown. As is shown in FIG. 2, the deconstructive manufacturing method begins with the purchase of the metal portion of the abutment from a manufacturer. The abutment analog is located in a model of the patient's mouth and the metal portion (analog) of the abutment, which is located in the model, is scanned. The data from the scan is then utilized to manufacture the ceramic portion of the abutment and the Core that fits around the ceramic portion of the abutment.

Figure 2A:
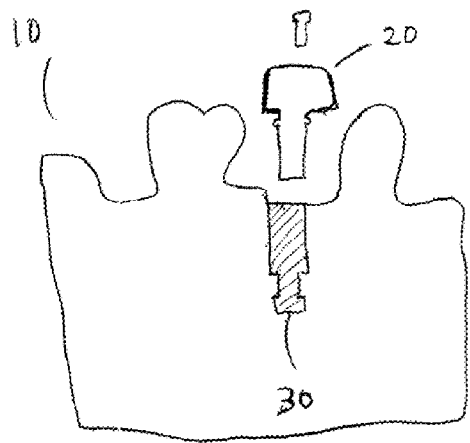
FIGS. 2a and 2b are partial front views of a master model implant analog utilized in accordance with an embodiment of the instant invention.
Figure 2B:
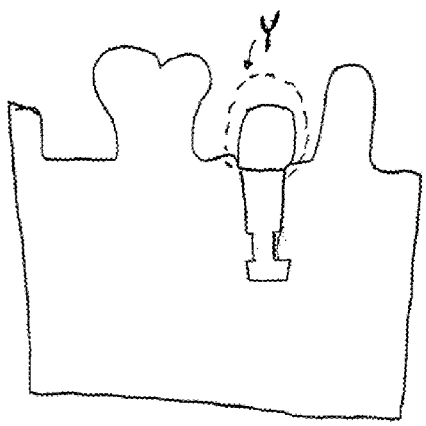

As is shown in FIGS. 2a and 2b, when a patient requires a tooth replacement, a three-dimensional model 10 of the patient's mouth is prepared. Using the model of the patient's mouth, a lab technician will fit the metal portion 20 of the abutment into the appropriate location 30 in the model. The model will then be scanned. As is discussed above, the scanning will take place at the centralized design/manufacturing facility after the model has been shipped to the facility. The scan provides data about the orientation of the metal insert within the model of the mouth and also data about the existing teeth surrounding the position of the abutment. The data from the scan, along with stored data about the standard shape of the metal insert to which the ceramic portion is to be mounted, is used to determine and design the appropriate shape for the ceramic portion of the abutment. At the same time, the shape of the Core (coping/infrastructure) is internally designed, using the data so that the Core (coping/infrastructure) will fit over the designed ceramic portion of the abutment.

Figure 3:
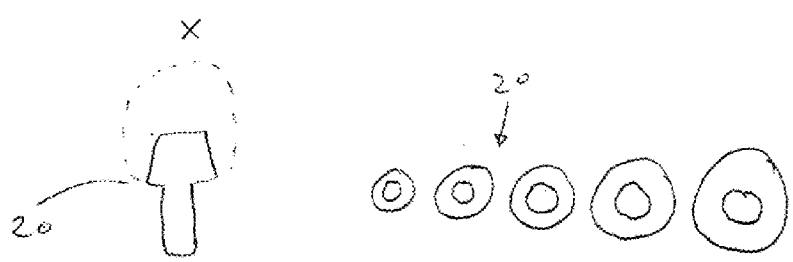
FIG. 3 shows front and top views of an implant base portion.
Figure 4:
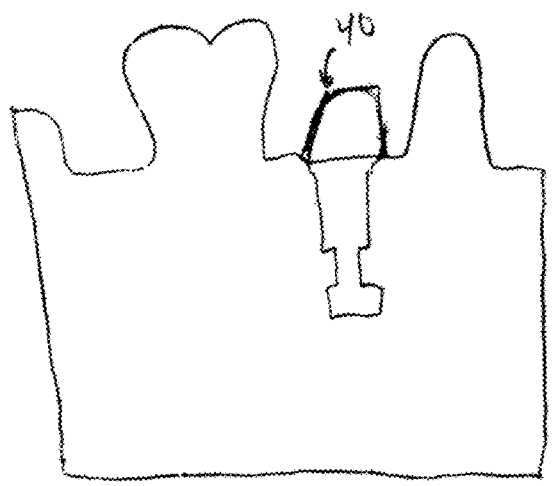
FIG. 4 shows a ceramic abutment portion of an implant used in accordance with an embodiment of the instant invention and designed within the master model implant analog of FIGS. 2a and 2b.
Figure 5:
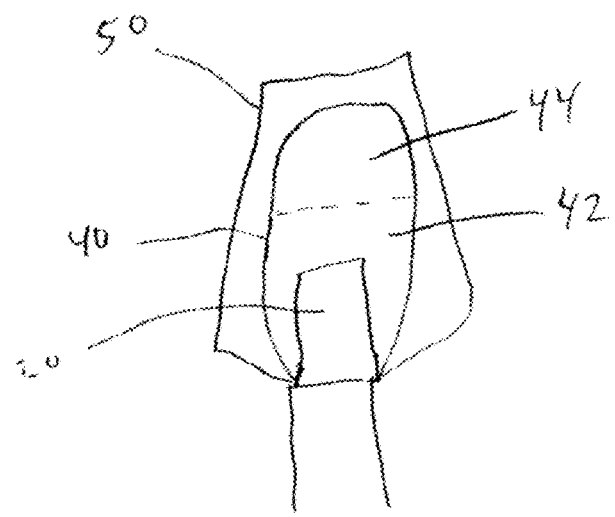
FIG. 5 shows the ceramic abutment portion of FIG. 4 and a Core designed to fit over the ceramic abutment portion.

Referring to FIGS. 2a, 2b, 3, 4 and 5, the process of manufacturing a custom crown Core (coping/infrastructure) and the ceramic portion of the abutment from a factory sintered block is shown. In the embodiment shown, the custom ceramic portion of the abutment and custom crown Core (coping/infrastructure) is made for use with an off-the-shelf lower abutment portion, such as the lower metal portion (Ti-base) of the Camlog Implant System. Information regarding the size and shape (X) of the off-the-shelf pieces are stored in a data file or library accessed by a milling machine (such as a DCS milling machine) or otherwise accessed by the central control system during the design phase. For example, as is shown in FIG. 3, information regarding size and shape X for five diameters of implants is shown. The implant analog of the Ti-base 20 is placed in a master model implant analog 10 and the model is scanned to obtain data about the orientation of the base within the model (such as the 3-dimensional axis) and data about the existing teeth surrounding the position of the base within the model (such as the interdental/arch Y information). The data from the scan, Y, is combined with the stored size and shape information regarding the Ti-base, X, to design a custom ceramic portion of the abutment 40 to fit over the Ti-base 20 and a custom crown Core 50 to fit over the custom ceramic portion of the abutment 40. The custom ceramic portion of the abutment 40 will be designed to have predetermined minimum dimensions 42 (stored in library) based upon the size and shape of the Ti-base being used. In most instances however, the actual custom ceramic abutment portion will have dimensions greater than the library-stored "minimum", thus the dimensions of the ceramic abutment portion 40 will include a wax-up 44 from the minimum dimensions 42. Once the final dimensions for the ceramic abutment portion 40 and the custom crown Core 50 are determined by wax-up software, the ceramic abutment portion and Core pieces are milled from a block of material.

Figure 6A:
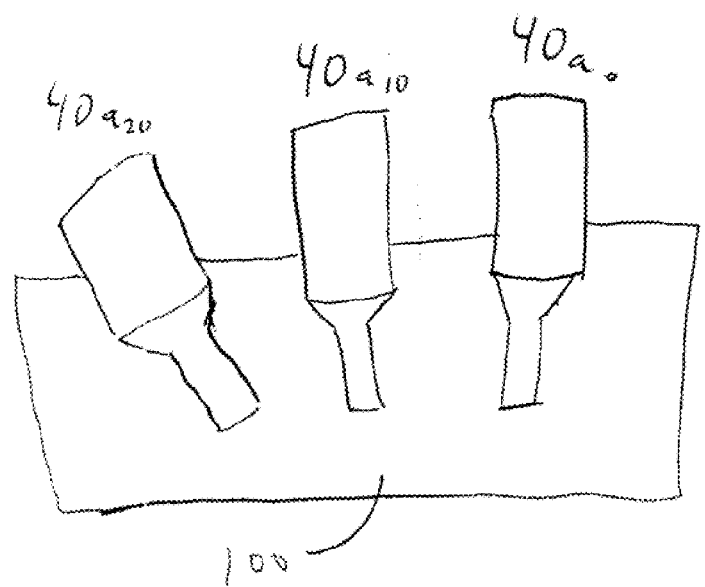
FIGS. 6a and 6b show a DCS frame used in accordance with an embodiment of the instant invention.
Figure 6B:
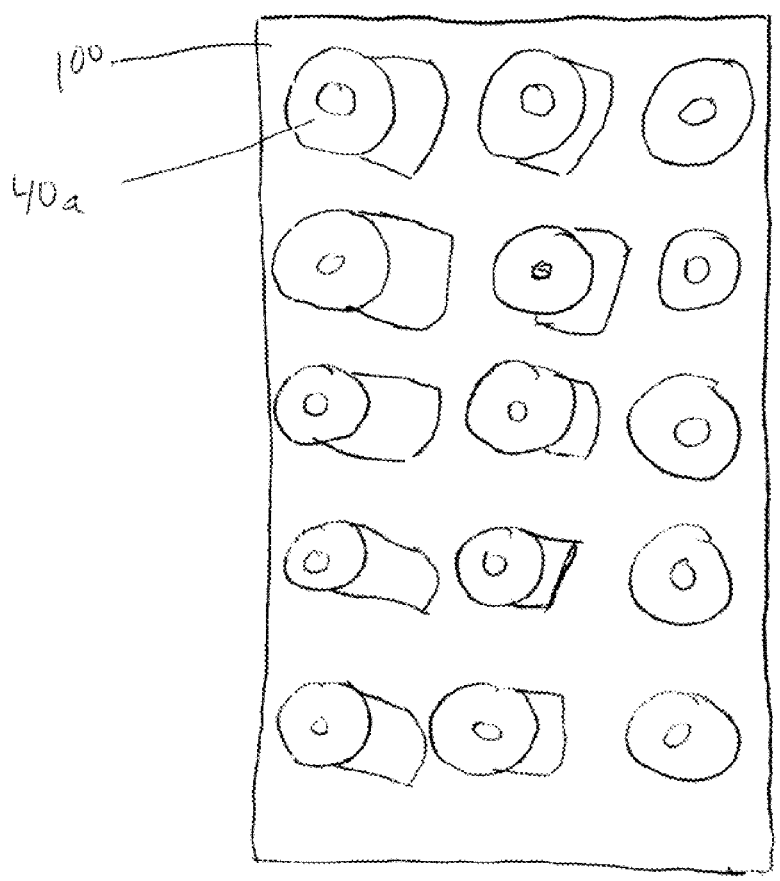

In an alternative embodiment, rather than milling abutment portion 40 and Core 50 from a single block of material, the abutment portion and Core (coping/infrastructure) may be milled out of separate pieces of material. Referring to FIGS. 6a and 6b, one such embodiment is shown and described, in which the material for the abutment portion 40 is retained within a frame 100 for support during milling. Frame 100 is designed for use in a single axis milling machine, such as a DCS milling machine, to accomplish milling of custom abutment portions. Frame 100 includes a molded/milled polymer base 110 which holds a threaded base 120 to which a blank 40a for the custom crown abutment portion 40 is attached. The frame is placed within the milling machine, and one of three angled blanks is chosen by control software of the machine depending upon the desired shape of the custom crown abutment portion 40 that is to be machined. This allows for undercutting of the blank which may be necessary for custom crown abutment portion that will be located at a variety of angled orientations. Implants having a generally orthogonal orientation will generally utilize the 0 degree blank, $40a_0$, for milling. As the orientation angle increases to about 10 decrees from an orthogonal orientation, the 10 decree blank, $40a_{10}$, will be utilized. As the orientation angle increases to about 20 degrees from an orthogonal orientation, the 20 decree blank, $40a_{20}$, will be utilized. Because additional material is needed to provide the "minimum" dimension of the custom abutment portion in angled orientations, the diameters of the blanks increase as the angle increases (i.e. 10 degree blank is larger diameter than 0 degree blank, and 20 degree blank is larger diameter than 10 degree blank). Once (or, in a preferred embodiment at the same time and on a different machine as) custom crown abutment portion 40 is milled, the design file is utilized to mill the Core (coping/infrastructure) from a separate block of material.

Once crown abutment portion 40 and Core 50 are milled, whether from a single piece of material, or from separate pieces, abutment portion 40 and Core 50 are hand finished.

In prior art systems, the custom dental crown Core (coping/infrastructure) and abutment are manufactured from the ground up. The abutment is designed first and the Core (coping/infrastructure) is designed to fit the abutment. In the instant invention the custom dental crown Core and abutment can be manufactured from the ground up by first determining the shape and orientation of the abutment and then determining the shape and orientation of the Core (coping/infrastructure).

Alternatively, the custom dental crown Core and abutment of the instant invention can be manufactured from the end product. In such a manner, the model is scanned and the shape and orientation of the final crown is determined or visualized by design software of the instant invention. The thickness for the crown is subtracted or deconstructed from the final shape of the substructure. First the thickness for the crown is subtracted from the final shape of the crown by the design software to determine the shape and orientation of the Core. The thickness of the Core (coping/infrastructure) is then subtracted to form the shape and orientation of the abutment. In one such an embodiment, the part of the final shape of the restoration that is subtracted is determined to maximize the aesthetic appearance of the final restoration by concealing the substructure. In one such embodiment, the software constructs a "mesh framework of point clusters" that are external to (or in addition to) the point clusters established by the scan of the original piece that is being restored (or scan of a model of the piece to establish the desired external appearance of the restoration). These point clusters are used to construct an image of a "concentric" substructure (concentric to the original piece) for the restoration. The operator then embellishes or diminishes certain key areas, after rendering of the substructure image, to design the final substructure shape. Once the basic, overall shape has been rendered, the computer then knows in 3d, through the point clusters, where the operator is working, allowing the operator to easily take away portions of the image to result in a final image for the substructure.

Although shown and described above in connection with manufacturing a crown implant, it will be appreciated that the methods of the instant invention can be used in connection with manufacturing of any dental restorations, including crowns and/or bridges, and including implant infrastructures and/or restorations supported by teeth. Further, it will be appreciated that the materials used to manufacture the Cores (copings/infrastructures) and abutements (as well as the veneer) of the instant invention are not limited to those described herein. Although the inventive method is particular well suited for use with Cores and abutements manufactured of zirconium and other comparable ceramics, the inventive method may be utilized in connection with Cores and/or abutements manufactured from any other suitable material (such as titanium) without departing from the spirit and scope of this instant invention. Furthermore, it will be appreciated that the inventive method may be utilized to manufacture Cores ("substructures"—as that term is used in the referenced application) of the type described in U.S. application Ser. No. 11/107,519 filed Apr. 15, 2005, the entire disclosure of which is incorporated herein by reference. It will further be appreciated that the method of the instant invention may be utilized in combination with a continuous production method as is described in U.S. application Ser. No. 11/023,950 filed Dec. 28, 2004, the entire disclosure of which is incorporated herein by reference.

The preferred method of the instant invention utilizes CAD-CAM design software, nevertheless, it will be appreciated other means of design (such as free-hand design, hologram or virtual reality modeling) now known or hereafter developed can be utilized in connection with the inventive method without departing from the spirit and scope of the instant invention. Further, it will be appreciated that the inventive method may be used in connection any manufacturing process for crowns or bridges now known or hereafter discovered, including but not limited to simultaneous milling of a Core (coping/infrastructure) and implant abutment, milling the coping (coping/infrastructure) and abutment as a single piece, or milling of crowns and bridges from blocks or rods, etc. In addition, it will be appreciated that the methods of the instant invention may utilize various means of manufacturing pieces other than the milling discussed herein. Alternative methods include but are not limited to press, stereo-lithograph build-up, lay-up, green ware production and subsequent milling or hand finishing.

In one embodiment of the instant invention, a software application of the central control system creates a custom Core and/or bridge Core design with minimal input from the operator of the software. Many of the typical design parameters required for the creation of the Core (coping/infrastructure) and/or bridge Core are stored in configuration settings or libraries/databases of the software application. The software application receives multiple polygon files from a scanner (such as a HyTech CT scanner). The files typically include scan data for the operative arch and may also include scan data for the opposing arch of the patient (or model). In a preferred embodiment, the scan data is mechanically aligned by the software such that the operative arch and the opposing arch are in the correct orientation relative to one another. In a preferred embodiment, the software will output files (such as STL or IGES) suitable for processing by "off-the-shelf" CAM packages. In another preferred embodiment the model file, bounding box dimensions and a patient ID (such as an ID number, which may be provided by the data from the packaging/transfer system of the instant invention) are stored in a database accessible by the software for later use.

In an embodiment of the software application, the software allows the user to specify an input directory in which patient scan data is located. The software opens the scan data files and utilizes that data to design the Core and abutment, or other pieces. In a preferred embodiment, the naming convention of scan data files, file folders, and/or other file identifiers are used to establish the basis for a patient ID for finished models. In one such embodiment, the patient ID is marked onto pieces during the manufacturing process in the same or similar manner as described in U.S. application Ser. No. 11/023,950 for easier identification.

In a preferred embodiment of the software, the software provides the operator tools to clean-up the model perimeter (i.e. trim excess data from around the operative and opposing arches), and for hole filling (i.e. all holes, excluding the perimeter of the operative and opposing arches are filled to show curvature of the preparation area). These may be optional procedures that are utilized when the condition of the input data so requires. These optional procedures may be initiated and performed automatically by the software based upon predetermined verification algorithms, or alternatively, may be manually initiated and/or performed by the operator after reviewing the scan data.

Figure 7:
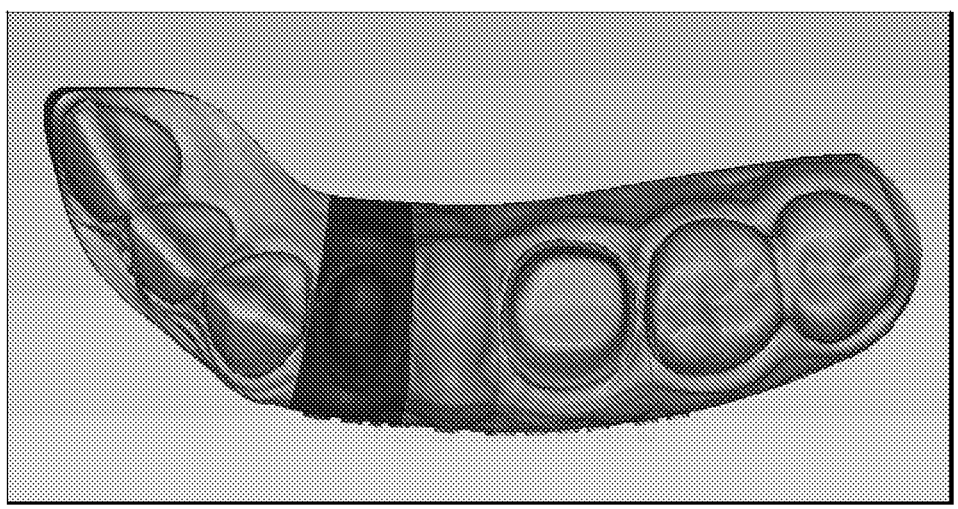
FIG. 7 shows a top view of a die-cut and ditched patient model.

In a preferred embodiment of the software, the models are die-cut and ditched prior to scanning (as is shown in FIG. 7) to identify all individual restorations to be designed and manufactured for the operative arch. Nevertheless, in one preferred embodiment, although die-cut and ditched prior to scanning, all the pieces are scanned in a single process and are individually identified by the software. Identification of the operative arch, the prepared teeth and the opposing arch are obtained by the software as design input. Depending upon the restoration being designed (i.e. whether a single tooth is being replaced, multiple teeth, a bridge, etc.), the software may utilize one or more tooth libraries that are selected automatically by the software or manually by the operator to be used to visualize the final external shape of the restoration.

The software of the instant invention may be utilized to design and manufacture individual Cores or bridges/bridge Cores. In an embodiment in which an individual Core is designed, the software automatically adds a cement gap having a thickness that is specified in the user configuration file as an offset to create the interior surface of an individual Core. The software further includes a tool (either automated or manual by operator) for undercut removal to ensure the interior surface of Core has a valid insertion angle. In a preferred embodiment a minimum tool radius compensation of 0.25 mm is applied to the interior surface. The software application further includes an undercut reporting feature. If additional grinding is required after milling to remove excessive undercuts a report is generated by the software application to notify the dentist of the need to perform additional grinding and indicating the location and amount of material to be removed.

In a preferred embodiment, the software designs the exterior surface of the Core (coping/infrastructure) based upon a tooth shape library. The exterior of the Core is created by first approximating the geometry of the fully restored tooth. In a preferred embodiment, multiple libraries are included for multiple tooth shapes. In a preferred embodiment, the software automatically determines the geometry of the tooth based upon the geometry of the teeth surrounding the restoration area. The software include algorithms to help automatically determine from the libraries the best or preferred geometry of the restoration based upon predefined criteria. For example, the predefined criteria may specify that teeth located at a certain location of the operative arch have a certain general shape and spacing from other teeth. The criteria may be built into and predefined in the software of the instant invention. In an alternative embodiment, at least certain criteria may be customized and controlled by the user of the software. In another embodiment of the invention, the software adaptively learns from prior design processes to update the criteria based upon data from the prior design processes. For example, the original criteria might specify a diameter between a certain relatively broad range. As the software designs multiple restorations, the software narrows the range based upon an evaluation and/or averaging of the actual data for the designs.

Using the appropriate geometry from the library the tooth is located over the central axis of the stump (preparation, abutment, etc.) by the software. The tooth is scaled based upon inter-proximal distance and the distance to the opposing arch. In cases where multiple preparations exist proximally to one another the software will decide the best way to divide (allocate) the inter-proximal space.

Figure 8:
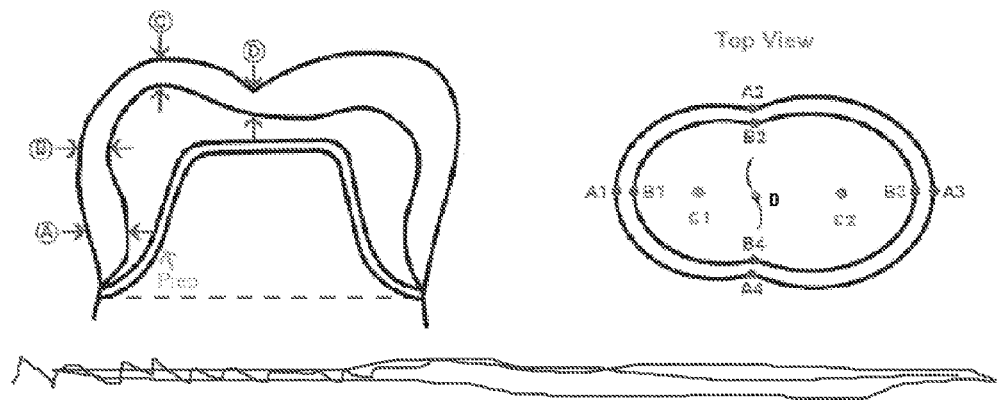
FIG. 8 shows front sectional and top views of a tooth reconstruction.

In a preferred embodiment of the software, a non-uniform offset of the reconstructed tooth is used to create the exterior surface of the Core (coping/infrastructure). Porcelain thickness values at certain user defined points (as shown in FIG. 8) establish the correct offset parameters In one embodiment, a fixed offset is used for the occlusal surface, and the Core (coping/infrastructure) is tapered to the margin. In such an embodiment, the software maintains a minimum margin line thickness for machining purposes.

In a preferred embodiment, the software includes manual editing tools for use by the operator. Should fully parametric modeling of the coping fail to produce an acceptable result the software will provide tools for manual editing of the coping shape. In one embodiment, the standard tools include scaling (both symmetric and non-symmetric) and a virtual wax knife tool to add remove or smooth material on the exterior surface.

In one preferred embodiment, the software adds or allows an operator to add a support ring structure to each Core (coping/infrastructure), either manually or automatically, in the manner described in U.S. application Ser. No. 11/107, 519.

The Core (coping/infrastructure) design parameters of the software described above will also be utilized in bridge designs (in addition to individual preparations). Core Design for bridges is virtually identical to that for single units except for the insertion angle calculation. Undercut removal and insertion angle is calculated by the software by considering each preparation in the bridge as a single entity.

Pontics from a user specified library will be placed automatically by the software.

Pontics are selected from multiple pontic libraries accessible by the software. Each pontic will have specified connection points determined by the software to facilitate automatic connector alignment.

The pontics of the bridge are automatically scaled and aligned by the software such that the curve of the operative arch is maintained. In one embodiment, non uniform scaling of the pontic is required to achieve desired offset from the opposing arch and the gingival surface.

Should fully parametric modeling of the pontic fail to produce an acceptable result the software includes tools for manual editing of the pontic size, shape and position. The standard tools include scaling (both symmetric and non-symmetric), translation and rotation handles, and a virtual wax knife tool to add remove or smooth material on the exterior surface.

Filleted connectors are constructed automatically by the software between all Cores (coping/infrastructure) and pontics. A minimum cross-section, specified in the design configuration settings is maintained. In a preferred embodiment, the software accesses a connector library to select the appropriate design.

Should fully parametric modeling of the connector fail to produce an acceptable result the software provides tools for manual editing of the connector size, shape and position. The standard tools include scaling (both horizontal and vertical), and a shaping tool for custom connector design.

In one preferred embodiment, the software adds or allows an operator to add a support ring structure to each Core (coping/infrastructure), either manually or automatically, in the manner described in U.S. application Ser. No. 11/107, 519. In a preferred embodiment, the support structure is a user-defined geometry that is added to the exterior of the Core. The placement and size of the feature is parametrically defined in a configuration file.

In a preferred embodiment of the software, a bounding box calculation is used to determine the minimum size material blank from which the design can be machined. The bounding box of the design is added to any tool radius compensation to calculate the total material required.

In one embodiment, compensation for material shrinkage is input in the software application by the user on a lot by lot basis. When pre-sintered material is used the scaling will be zero.

In a preferred embodiment, the final model for Cores (copings/infrastructures) or bridge Cores is output in a format suitable for input to a CAM package. IGES or STEP are the preferred formats. STL output formats may also be supported.

To the extent possible, data processing by the software is fully automated. Where user input is required it is 'front-end' loaded such that the operators are not required to wait for the completion of any processing to provide further input. It is recognized that some steps in the process will likely require some amount of user intervention. By placing these steps at the beginning of this process the operator will require minimal hands-on editing for most cases. In a preferred embodiment, user required inputs are stored in a file to enable batch processing of multiple datasets.

In a preferred embodiment of the invention, the bounding box of the design is added to any tool radius compensation to calculate the total material required.

In one embodiment, if the tooth ID information is not available from the scan data file, the software requires the user to guide the program in identifying prepared teeth with on-screen selections. Basic prescription information will also be entered.

In a preferred embodiment a fully automated initial virtual tooth replacement (or edentulous space, prepared tooth or implant in edentulous space) will be calculated for individual Cores (copings/infrastructures) and multi-unit bridge Cores based upon the scan data and the teeth surrounding the restoration (in the manner discussed above). Once the virtual tooth replacement is calculated, the Core is deconstructed in the manner discussed above.

In one embodiment, the finished restoration is displayed by the software along with the stumps (abutment, preparation, etc.) and opposing bite. Analytical tools (distance to neighbors, opposing bite, etc.) is used to help the operator determine if the restoration is acceptable.

In a preferred embodiment of the software, only if the restoration is found to be unacceptable will manual editing be required. Standard editing tools allow modification of margin line, Core (coping/infrastructure) design, pontic placement, connector design and general wax-knife.

In a preferred embodiment, the bounding box of the design is added to any tool radius compensation to calculate the total material required for any 4+ Unit Bridge processes. In one embodiment, if the tooth ID information is not available from the scan data file, the user will guide the program in identifying prepared teeth with on-screen selections. Basic prescription information will also be entered.

For problematic (i.e. where a design parameter goes outside of predetermined boundaries stored in the database or libraries) restorations the automated section of the program will terminate in manual editing mode. Standard editing tools allow modification of margin line, Core (coping/infrastructure) design, pontic placement, connector design. A generic wax-knife editing tool will also be available. The bounding box of the design is added to any tool radius compensation to calculate the total material required In all software embodiments discussed above, completed design files are saved for manufacture. In a preferred embodiment, the data in the stored digital/electronic files are accessed and utilized by the software application to aid in the design and/or manufacture of "companion" or "collateral" components, such as implant abutments (made from file data regarding the inside of the crown Core), provisional acrylic splints/temporaries (made from data regarding the whole final restoration/tooth shape), Core overlays (made from data regarding the exterior of the crown Core), super-molds to form first stage ceramics on Cores, simultaneous abutments to fit under Cores, other digital/graphic driven services, etc. As used herein, companion components refer to components that mate together with each other, while collateral components refer to peripheral pieces, such as molds, that are used to make a final piece that mates together with other components of a restoration.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A method of Mass Custom Manufacturing of dental crowns and crown components comprising the steps of:

obtaining a single master electronic file including a virtual model including a final external shape of a virtual ideal tooth replacement of a restoration for a patient;

utilizing said master file to manufacture in a coordinated, sequential, simultaneous or partly simultaneous and partly sequential, manner, from end-stage materials, two or more components of a single artificial tooth of a dental restoration; and wherein said two or more components of said dental restoration mate together to make up a single artificial tooth of a dental restoration; or wherein at least one of said two or more components is utilized to make one or more pieces that mates together with at least one other of said two or more components to make up a single artificial tooth of a dental restoration.

2. The method as claimed in claim 1 wherein at least one of said components is a collateral component.

3. A method of making a plurality of prosthodontic pieces sized for positioning within a patient's mouth, said method comprising the steps of:

providing information to a machine for manufacturing dental crowns or crown components regarding a crown or component to be manufactured;

operating said machine to manufacture individual crowns or crown components from a stock material that is fed into the machine;

operating said machine to place a unique identification mark on each crown or crown component as it is manufactured by said machine; and using said identification mark to avoid confusion between a plurality of individual crowns or crown components produced.

4. The method as claimed in claim 3 wherein the plurality of individual crowns or crown components produced are manufactured by multiple different machines at a central Mass Custom Manufacturing facility.

5. The method as claimed in claim 3 further comprising the step of inspecting for quality each crown or crown component that is manufactured and packaging the crown or crown component following said inspection step.

\* \* \* \* \*